United States Patent [19]

Morimoto et al.

[11] Patent Number: 5,240,932
[45] Date of Patent: Aug. 31, 1993

[54] PERCUTANEOUSLY ABSORBABLE COMPOSITIONS OF MORPHINE OR ANALOGOUS ANALGESICS OF MORPHINE

[75] Inventors: Yasunori Morimoto, 7-22, Nishisakado 4-chome, Sakado-shi, Saitama-ken, 350-02, Japan; Kenji Sugibayashi, Sakado; Kouji Kobayashi, Tokyo; Hisashi Kusano, Ageo, all of Japan

[73] Assignee: Yasunori Morimoto, Sakado, Japan

[21] Appl. No.: 781,226

[22] PCT Filed: Mar. 29, 1991

[86] PCT No.: PCT/JP91/00413
§ 371 Date: Jan. 7, 1992
§ 102(e) Date: Jan. 7, 1992

[87] PCT Pub. No.: WO91/15241
PCT Pub. Date: Oct. 17, 1991

[30] Foreign Application Priority Data

Mar. 30, 1991 [JP] Japan .................................. 2-81180

[51] Int. Cl.$^5$ ............................................. A61K 31/44

[52] U.S. Cl. .................................... 514/282; 514/946; 514/947

[58] Field of Search ......................... 514/282, 946, 947

[56] References Cited

PUBLICATIONS

Chem. Abst. 80: 116160h (1974).
Chem. Abst. 93: 20542b (1980).
Chem. Abst. 104: 213272t (1986).

*Primary Examiner*—S. J. Friedman
*Attorney, Agent, or Firm*—Spencer, Frank & Schneider

[57] ABSTRACT

A composition which is percutaneously absorbable, including a narcotic analgesic selected from the group consisting of morphine and analogous analgesics thereof; from 1 to 20 weight percent of a percutaneous absorption accelerator comprised of one of (a) a terpene and (b) an essential oil; from 10 to 60 weight percent of a percutaneous absorption accelerating assistant comprised of one of (a) a lower alcohol having 1-5 carbon atoms, (b) water and (c) a lower glycol having 2-5 carbon atoms.

10 Claims, 11 Drawing Sheets

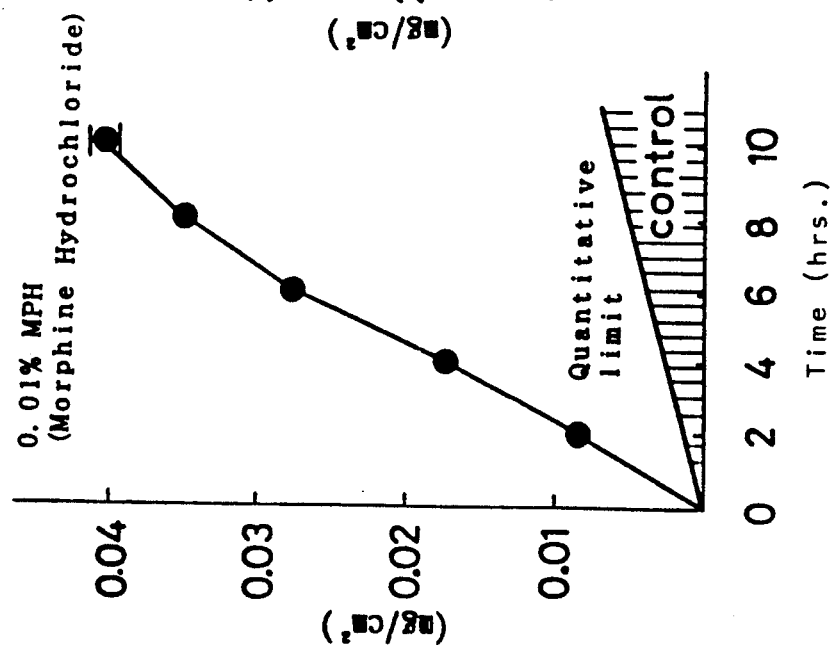
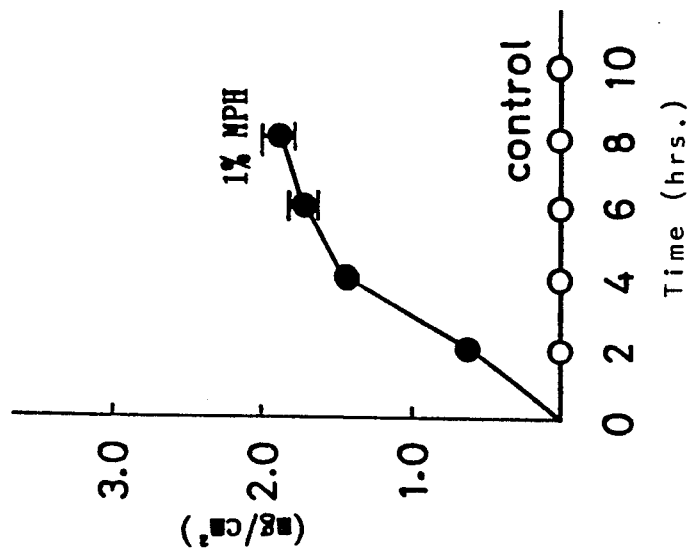
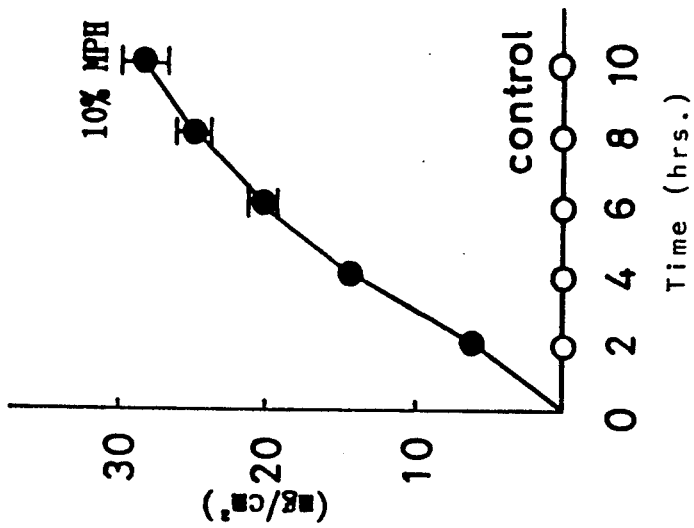
Fig. 2(a)
Fig. 2(b)
Fig. 2(c)

PERCUTANEOUSLY ABSORBABLE COMPOSITIONS OF MORPHINE OR ANALOGOUS ANALGESICS OF MORPHINE

BACKGROUND OF THE INVENTION

1. Field of the Invention

The present invention relates to percutaneously absorbable formulations such as analgesics such as morphine, or its salts or bases.

2. Background of the Related Art

Narcotic analgesics such as morphine or its salts and nonnarcotic analgesics such as eptazocine have been orally administered or injected to ease postoperative and cancerous pains.

In the case of such injecting agents, at-home treatment is difficult because of the necessity of administration by a third person, and further medicines having short working times such as morphine are disadvantageously difficult to administer at the time of acute pain because of its increased administration frequency.

Oral agents, which have been developed for the purpose of simplification of administration and use, overcame some disadvantages of the injecting agents, but are not so much improved in working time, in which the migrating property and retentivity of the formulations in digestive organs are difficult to control even by pharmaceutical designs for gradual release, and the persistency has its limit.

Further, many cancer patients in the last stage can not have oral administration of analgesics because of vomiting and nausea which are the side effects of carcinostatic substances.

On the other hand, formulations applied to the skin have an expected persistency of medicinal effect of about 24 hours to 1 week for one administration, and are applicable to patients for which oral administration is not possible.

In general, medicines have low percutaneous absorbability, and it is the same with analgesics including morphine and its salts.

The main barrier to percutaneous absorption of medicines resides in a horny layer, and various accelerators have been developed as the accelerators were considered to increase the percutaneous absorbability to the lipids of the horny layer. However, the medicine permeability of the epidermis other than the horny layer becomes the barrier in simple absorption accelerators acting on the horny layer and combinations thereof, so that very excellent accelerators have not been developed yet.

In view of the disadvantages of the prior arts, as a result of the earnest studies on utilization of analgesics such as morphine, which were used only as injecting agents and oral agents in the past, for percutaneously absorbable type external agents such as ointment, cream, tape dressing, plaster dressing, patch dressing, and pap dressing (wet dressing), the present inventors have found and attained this invention.

SUMMARY OF THE INVENTION

The present invention can provide a percutaneously absorbable formulation by dissolving a percutaneously absorbable composition of narcotic or nonnarcotic analgesics into a base agent formed of a percutaneous absorption accelerator consisting of a terpene and/or an essential oil and a percutaneous absorption accelerating assistant consisting of a lower alcohol having 1–5 carbon atoms.

As the narcotic analgesics used in the present invention, morphine hydrochloride, ethylmorphine hydrochloride, morphine sulfate, cocaine hydrochloride, pethidine hydrochloride, codeine phosphate, dihydrocodeine phosphate, fentanyl citrate, sufentanil, meperidine hydrochloride and the like are used. As the nonnarcotic analgesics, eptazocine hydrobromide, buprenorphine hydrochloride, butorphanol tartrate, or other salts are used. These analgesics may be constituted by basic ones.

As the percutaneous absorption accelerators, hydrocarbon monoterpenes such as limonene, monoterpene alcohols such as l-menthol, terpineol and borneol, monoterpene aldehydes such as citral, monoterpene ketones such as ionone, other monoterpenes such as cineole, or essential oils containing monoterpenes such as mentha oil, peppermint oil, and eucalyptus oil are used.

As the percutaneous absorption accelerating assistants, lower alcohols having 1–5 carbon atoms such as methyl alcohol, ethyl alcohol, propyl alcohol, butyl alcohol, amyl alcohol, isopropyl alcohol and the like are used.

The blending quantities are varied depending on the kinds of medicines used, but the percutaneous absorption accelerator is preferably used in a ratio of 1–20 wt. % and the percutaneous absorption accelerating assistant in a ratio of 10–60 wt. %.

As other percutaneous absorption accelerators, alcohols having 8–22 carbon atoms, fatty acids having 8–22 carbon atoms, fatty acid methyl, ethyl, vinyl, n-propyl, isopropyl, propylene, n-butyl, isobutyl and buthylene esters having 8–22 carbon atoms, n-alkylpyrrolidones having 1–16 carbon atoms and/or mixtures thereof may be added.

Further, as other percutaneous absorption accelerating assistants, water, lower glycols having 2–20, preferably 2–5, carbon atoms such as glycerol and propylene glycol, lower ketones having 2–5 carbon atoms, or aldehyde may be added.

BRIEF DESCRIPTION OF THE DRAWINGS

FIGS. 1–11 are graphs showing the changes on standing of absorption quantities of medicines through the skin with various kinds and quantities of medicines, percutaneous absorption accelerators, and percutaneous absorption accelerating assistants related to the formulations according to the examples of the present invention and the formulations of comparative examples.

EFFECT

The percutaneous absorption accelerator in the composition physically removes the barrier ability of the horny layer of the skin and enhances the medicine permeability of the skin.

The percutaneous absorption accelerating assistant increases the solubility of the medicine and also medicine permeability, resulting in a remarkable improvement in absorbability of the medicine as a synergistic effect.

DESCRIPTION OF THE PREFERRED EMBODIMENTS

The present invention is further illustrated in detail according to following examples.

EXAMPLE 1

Formulations as shown in Table 1 were prepared, and comparatively examined for the change on standing of skin permeating quantity by means of a skin permeation test method described below.

Skin Permeation Test Method

The abdominal extracted skin of a hairless rat (male, body weight 150 g, available from Saitama Experimental Animals) was put in a 2-chamber diffusing cell (contact area: 1.0 cm$^2$) of a skin permeation test and held at 37° C. Then, 2.5 ml of a medicine solution was put on the horny layer side, and 2.5 ml of water on the derm side. Ten diffusing cell dermic solutions were sampled and the lapse of time, and the quantities of the medicine permeated through the skin after 2, 4, 6, 8 and 10 hours were measured. The results are as shown in Table 2 and FIG. 1.

TABLE 1

| Sample Component | unit: w % This Invention 1 | Comparative Example 1 | 2 | 3 |
| --- | --- | --- | --- | --- |
| Morphine hydrochloride | 1 | 1 | 1 | 1 |
| l-Menthol | 5 | — | — | 5 |
| Ethanol | 40 | — | 40 | — |
| Water | 54 | 99 | 59 | 4 |

TABLE 2

| | unit: μg/cm$^2$ | | | | | | | |
| --- | --- | --- | --- | --- | --- | --- | --- | --- |
| Time | This Invention 1 | | Comparative Ex. 1 | | Comparative Ex. 2 | | Comparative Ex. 3 | |
| elapsed | Mean | Deviation | Mean | Deviation | Mean | Deviation | Mean | Deviation |
| 2 | 629 | 20.9 | 1.72 | 0.25 | 3.58 | 0.52 | 10.2 | 3.73 |
| 4 | 1436 | 87.3 | 3.43 | 0.01 | 10.3 | 1.54 | 49.3 | 0.12 |
| 6 | 1732 | 90.9 | 6.34 | 0.23 | 23.0 | 5.59 | 161 | 10.1 |
| 8 | 1893 | 111 | 12.6 | 1.78 | 40.6 | 11.4 | 321 | 20.1 |
| 10 | — | — | 17.1 | 3.19 | 73.3 | 15.1 | 533 | 20.0 |

The results showed that the formation having l-menthol selected as an absorption accelerator and ethanol as an absorption accelerating assistant has excellent percutaneous absorptivity.

EXAMPLE 2

To examine the relation of the concentration of morphine hydrochloride with skin permeativity, formulations shown in Table 3 were prepared and examined on the basis of the skin permeation test.

TABLE 3

| Component | unit: w % This Invention 1 | 2 | 3 |
| --- | --- | --- | --- |
| Morphine hydrochloride | 1 | 10 | 0.01 |
| l-Menthol | 5 | 5 | 5 |
| Ethanol | 40 | 40 | 40 |
| Water | 54 | 45 | 54.99 |

Figure 1:
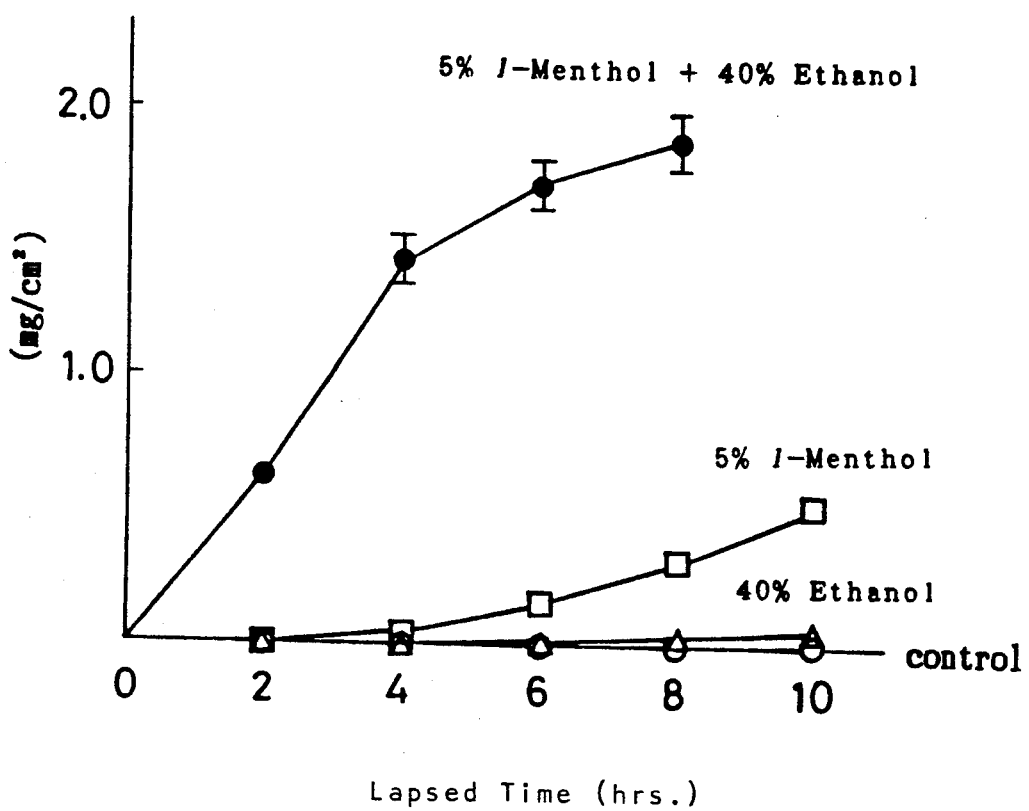
Figure 10:
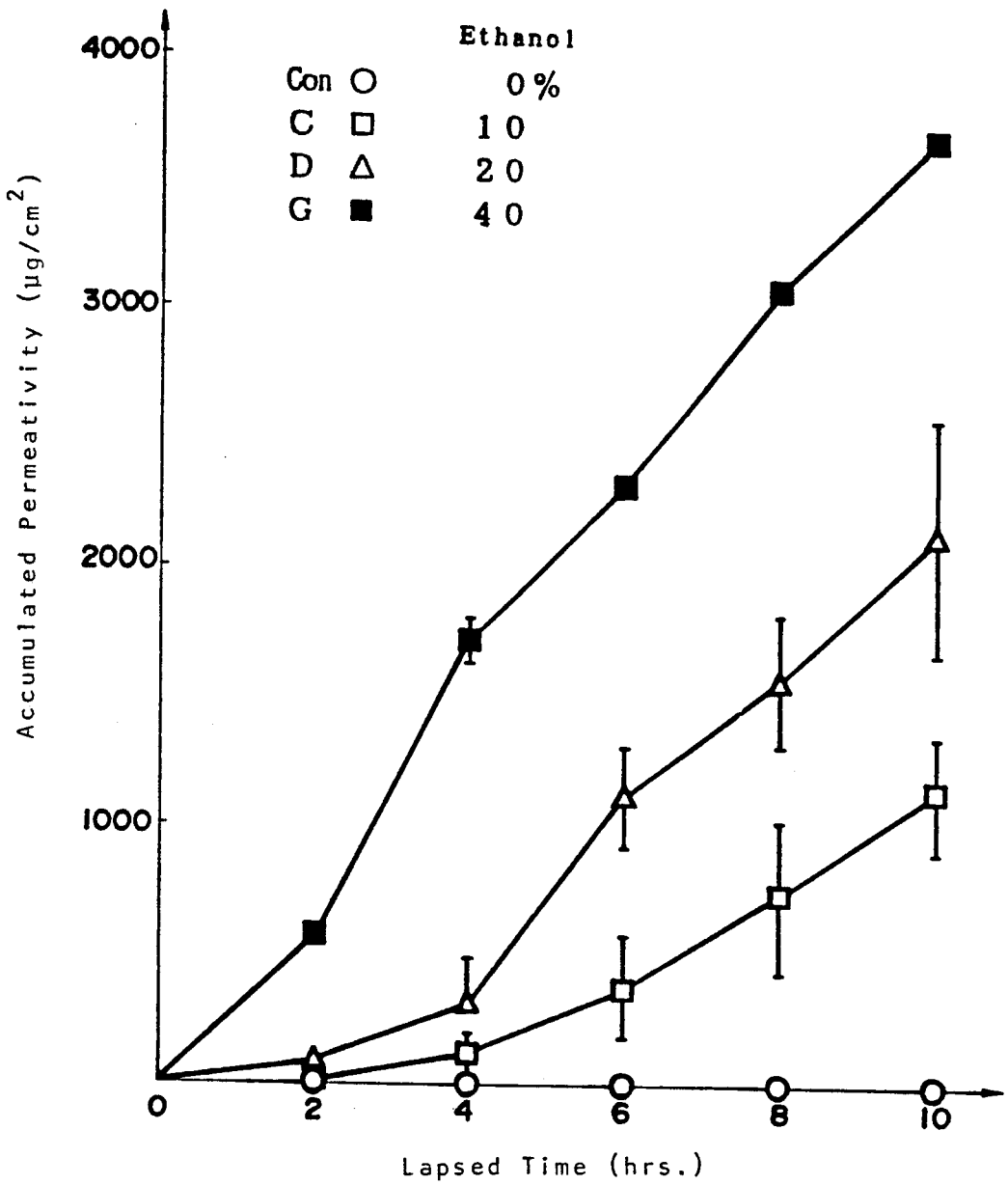

As shown in FIGS. 2(a), 2(b) nd 2(c), and Table 4, the results showed that the medicine is absorbed percutaneously corresponding to the concentration of morphine hydrochloride, i.e., 0.01 W % in FIG. 2(a), 1 W % in FIG. 2(b), and 10 W % in FIG. 2(c).

TABLE 4

| | unit: μg/cm$^2$ | | | | | |
| --- | --- | --- | --- | --- | --- | --- |
| Time | This Invention 1 | | This Invention 2 | | This Invention 3 | |
| elapsed | Mean | Deviation | Mean | Deviation | Mean | Deviation |
| 2 | 629 | 20.9 | 6256 | 213 | 8.45 | 0.08 |
| 4 | 1436 | 87.3 | 14399 | 671 | 17.4 | 0.34 |
| 6 | 1732 | 90.9 | 20323 | 940 | 27.7 | 1.03 |
| 8 | 1893 | 111 | 24958 | 1142 | 35.0 | 0.63 |
| 10 | — | — | 18410 | 1580 | 40.4 | 0.88 |

EXAMPLE 3

Formulations containing different kinds of percutaneous absorption accelerators were prepared as shown in Table 5, and comparatively examined for percutaneous absorbability of morphine hydrochloride in the same manner as in Example 1.

TABLE 5

| Component | unit: w % This Invention 1 | 4 | 5 |
| --- | --- | --- | --- |
| Morphine hydrochloride | 1 | 1 | 1 |
| l-Menthol | 5 | — | — |
| Terpineol | — | 5 | — |
| Peppermint oil | — | — | 5 |
| Ethanol | 40 | 40 | 40 |
| Water | 54 | 54 | 54 |

Figure 3:
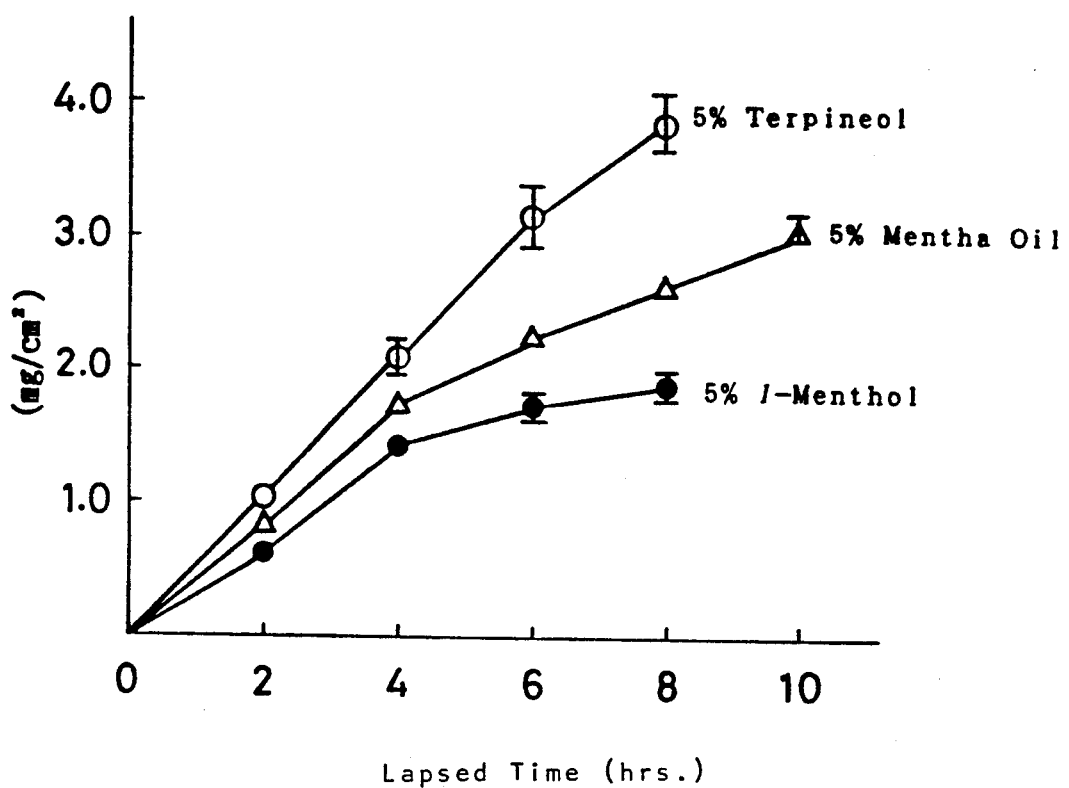

Consequently, as shown in FIG. 3 and Table 6, excellent percutaneous absorbability was shown for every percutaneous absorption accelerator, but particularly the best was terpineol.

TABLE 6

| | unit: μg/cm$^2$ | | | | | |
| --- | --- | --- | --- | --- | --- | --- |
| Time | This Invention 1 | | This Invention 4 | | This Invention 5 | |
| elapsed | Mean | Deviation | Mean | Deviation | Mean | Deviation |
| 2 | 629 | 20.9 | 1046 | 44.5 | 854 | 65.2 |

TABLE 6-continued

| Time | This Invention 1 | | This Invention 4 | | This Invention 5 | |
|---|---|---|---|---|---|---|
| elapsed | Mean | Deviation | Mean | Deviation | Mean | Deviation |
| 4 | 1436 | 87.3 | 2111 | 107 | 1766 | 64.7 |
| 6 | 1732 | 90.9 | 3163 | 226 | 2283 | 73.3 |
| 8 | 1893 | 111 | 3884 | 223 | 2662 | 93.8 |
| 10 | — | — | — | — | 3087 | 100 | unit: μg/cm²

EXAMPLE 4

To examine the effect of the concentration of l-menthol on the skin permeability of morphine hydrochloride from an l-menthol-ethanol-water system, formations as shown in Table 7 were prepared and examined for percutaneous absorbability.

TABLE 7

| Sample | This Invention | | | Comparative Ex. | |
|---|---|---|---|---|---|
| Component | 6 | 1 | 7 | 4 | 5 |
| Morphine hydrochloride | 1 | 1 | 1 | 1 | 1 |
| l-Menthol | 2.5 | 5 | 10 | 1 | 0.1 |
| Ethanol | 40 | 40 | 40 | 40 | 40 |
| Water | 56.4 | 54 | 49 | 58 | 58.9 | unit: w %

Figure 4:
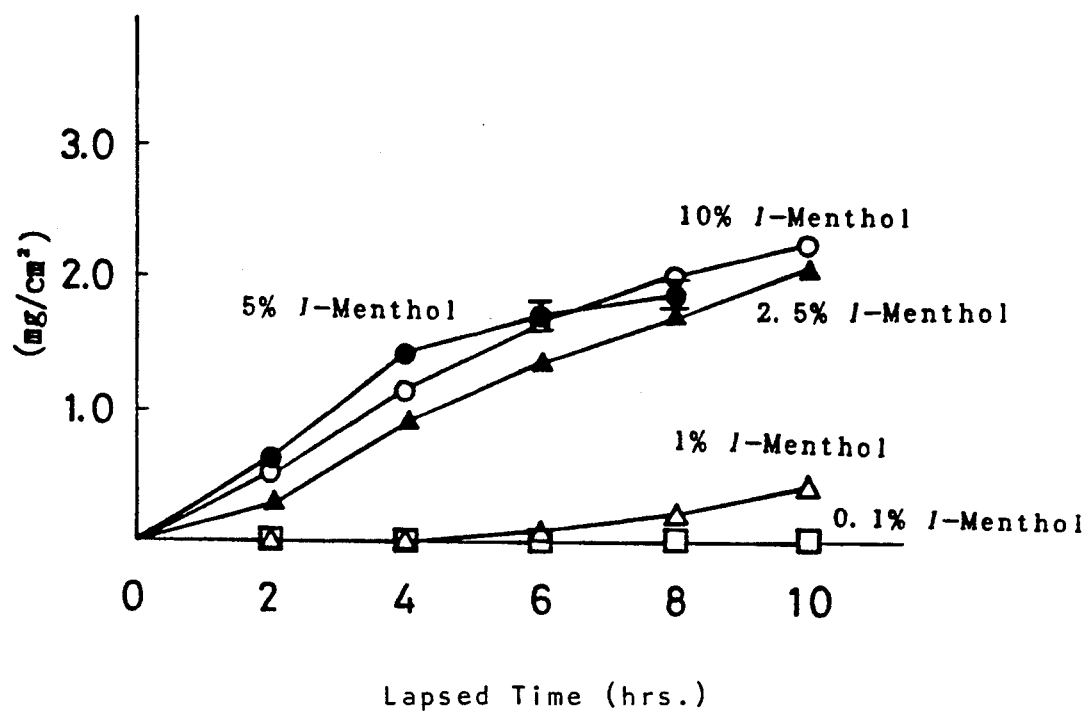

As shown in FIG. 4 and Table 8, the results showed that skin permeativity is excellent when the concentration of menthol is 2.5 w % or more.

TABLE 8

| Time | This Invention 1 | | This Invention 6 | | This Invention 7 | | Comp. Ex. 4 | | Comp. Ex. 5 | |
|---|---|---|---|---|---|---|---|---|---|---|
| elapsed | Mean | Deviation | Mean | Deviation | Mean | Deviation | Mean | Deviation | Mean | Deviation |
| 2 | 629 | 20.9 | 292 | 39.8 | 524 | 67.1 | 0.0 | 0.0 | 0.0 | 0.0 |
| 4 | 1436 | 87.3 | 876 | 47.4 | 1164 | 88.0 | 18.34 | 2.77 | 2.42 | 0.63 |
| 6 | 1732 | 90.9 | 1340 | 62.4 | 1665 | 94.8 | 83.4 | 15.5 | 6.90 | 1.27 |
| 8 | 1893 | 111 | 1717 | 57.8 | 2020 | 65.0 | 226 | 40.3 | 19.0 | 2.02 |
| 10 | — | — | 2057 | 71.9 | 2271 | 58.3 | 450 | 63.4 | 30.4 | 2.28 | unit: μg/cm²

EXAMPLE 5

To examine the effect of the concentration of ethanol, which is a percutaneous absorption accelerating assistant, on skin permeativity of morphine hydrochloride from an l-menthol-ethanol-water system, the formulations shown in Table 9 were prepared and examined for percutaneous absorbability.

TABLE 9

| Sample | This Invention | | | Comparative Ex. | |
|---|---|---|---|---|---|
| Component | 8 | 1 | 9 | 6 | 7 |
| Morphine hydrochloride | 1 | 1 | 1 | 1 | 1 |
| l-Menthol | 5 | 5 | 5 | 5 | 5 |
| Ethanol | 20 | 40 | 60 | 80 | 94 |
| Water | 74 | 54 | 34 | 14 | — | unit: w %

Figure 5:
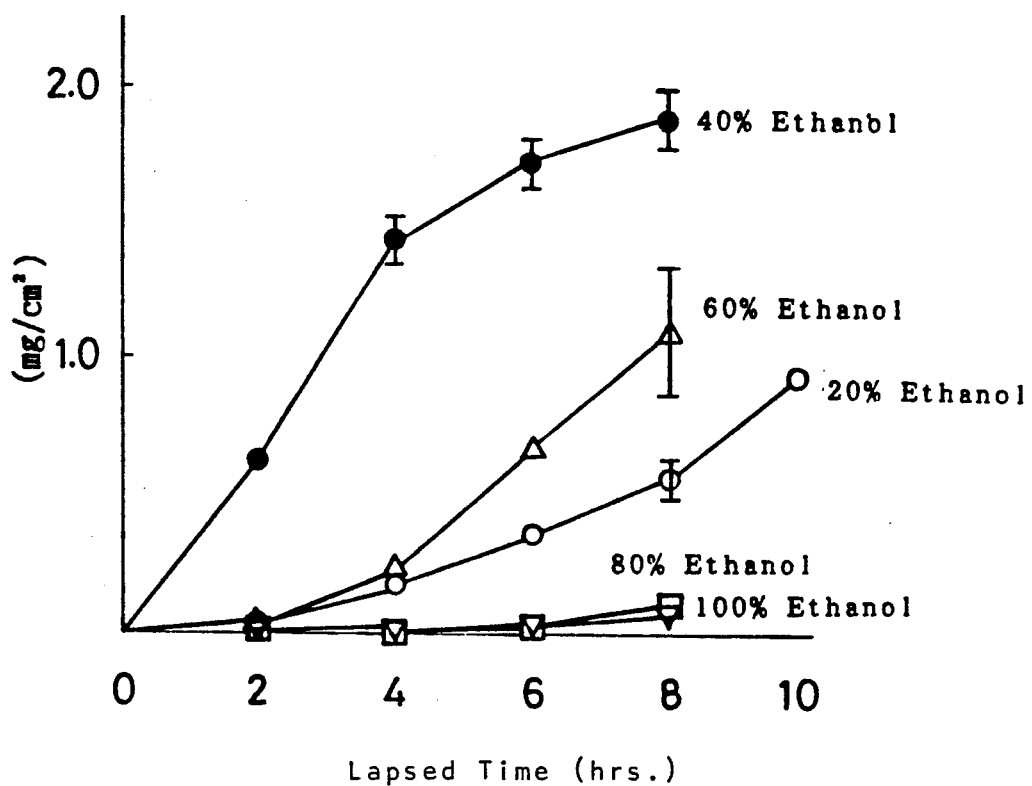

As shown in FIG. 5 and Table 10, the results showed that skin permeativity is excellent when the concentration of ethanol is 20 w % or more and less than 60 w %.

TABLE 10

| Time | This Invention 1 | | This Invention 8 | | This Invention 9 | | Comp. Ex. 6 | | Comp. Ex. 7 | |
|---|---|---|---|---|---|---|---|---|---|---|
| elapsed | Mean | Deviation | Mean | Deviation | Mean | Deviation | Mean | Deviation | Mean | Deviation |
| 2 | 629 | 20.9 | 45.0 | 4.08 | 15.9 | 2.0 | 0.72 | 0.7 | 0.76 | 0.76 |
| 4 | 1436 | 87.3 | 182 | 0.80 | 251 | 6.84 | 6.84 | 1.02 | 5.92 | 4.72 |
| 6 | 1732 | 90.9 | 366 | 18.3 | 688 | 33.6 | 33.6 | 0.13 | 25.8 | 18.6 |
| 8 | 1893 | 111 | 570 | 62.1 | 1106 | 226 | 104 | 0.29 | 66.6 | 46.3 |
| 10 | — | — | 942 | 87.4 | — | — | — | — | — | — | unit: μg/cm²

EXAMPLE 6

To examine the effect of the concentration of isopropyl alcohol (IPA), employed instead of ethanol, on skin permeativity of morphine hydrochloride from an l-menthol-alcohol-water system, the formulations shown in Table 11 were prepared and examined for percutaneous absorbability.

TABLE 11

| | This Invention | | |
|---|---|---|---|
| Component | 10 | 11 | 12 |
| Morphine hydrochloride | 1 | 1 | 1 |
| l-Menthol | 5 | 5 | 5 |
| Ethanol | 20 | 40 | 60 |
| Water | 74 | 54 | 34 | unit: w %

Figure 6:
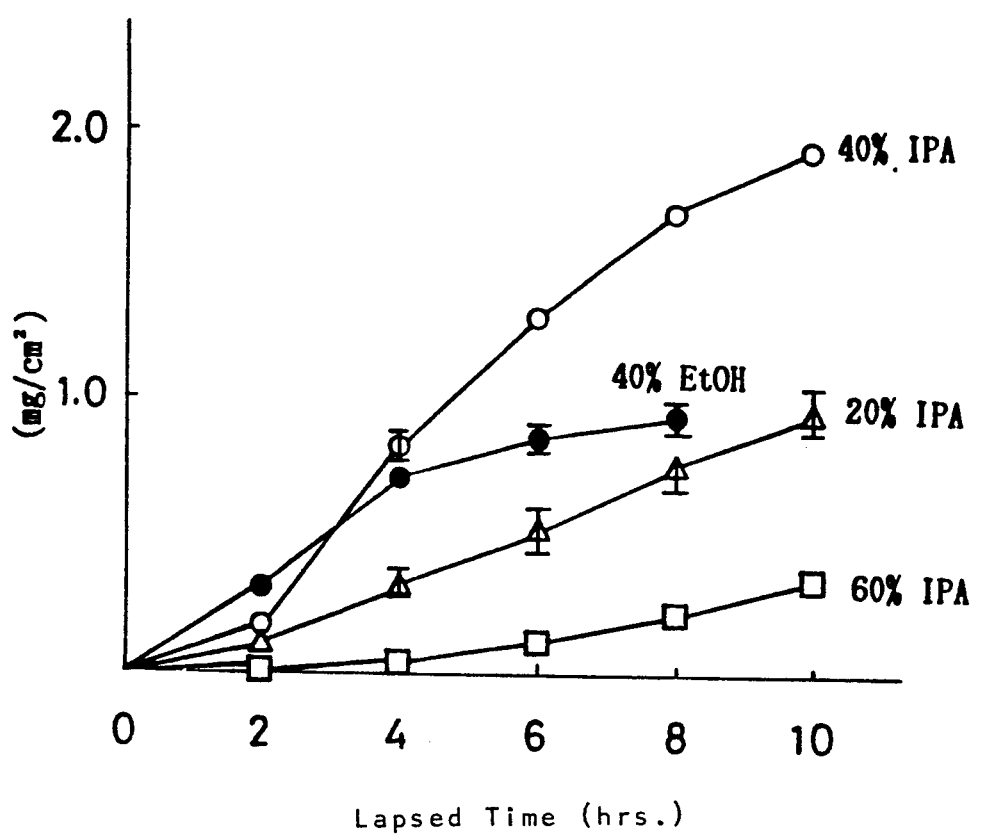

Consequently, as shown in FIG. 6 and Table 12, the skin permeativity was excellent when the concentration of isopropyl alcohol is 20 wt. % or more and less than 60 wt. % similar to the case of ethanol, and too high a concentration aggravated the absorbability.

TABLE 12 unit: μg/cm²

| Time elapsed | This Invention 1 | | This Invention 10 | | This Invention 11 | | This Invention 12 | |
|---|---|---|---|---|---|---|---|---|
| | Mean | Deviation | Mean | Deviation | Mean | Deviation | Mean | Deviation |
| 2 | 629 | 20.9 | 229 | 44.4 | 348 | 31.8 | 3.43 | 2.80 |
| 4 | 1436 | 87.3 | 665 | 94.7 | 1663 | 75.3 | 75.8 | 13.0 |
| 6 | 1732 | 90.9 | 1073 | 145 | 2624 | 68.2 | 227 | 32.6 |
| 8 | 1893 | 111 | 1546 | 184 | 3420 | 64.1 | 432 | 48.5 |
| 10 | — | — | 1922 | 178 | 3891 | 40.4 | 696 | 65.6 |

EXAMPLE 7

Instead of water added as the supplement to ethanol for the percutaneous absorption accelerating assistant having an influence on skin permeativity of morphine hydrochloride from an l-menthol-alcohol-water system, glycerol was mixed as shown in Table 13, and this was comparatively examined for percutaneous absorbability.

Figure 7:
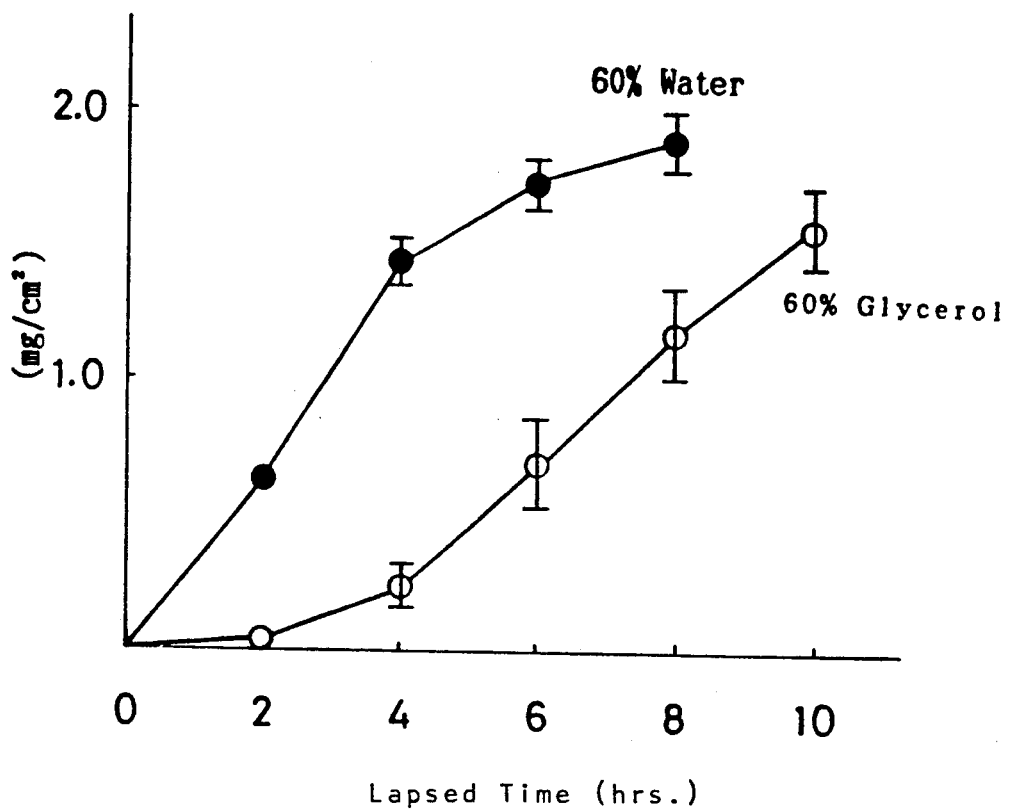

As shown in FIG. 7 and Table 14, the results showed that a percutaneous absorbability similar to that for water can be held when glycerol is used.

TABLE 13 unit: w %

| Sample Component | This Invention | |
|---|---|---|
| | 1 | 13 |
| Morphine hydrochloride | 1 | 1 |
| l-Menthol | 5 | 5 |
| Ethanol | 40 | 40 |
| Water | 54 | — |
| Glycerol | — | 54 |

TABLE 14 unit: μg/cm²

| Time elapsed | This Invention 1 | | This Invention 13 | |
|---|---|---|---|---|
| | Mean | Deviation | Mean | Deviation |
| 2 | 629 | 20.9 | 26.8 | 8.40 |
| 4 | 1436 | 87.3 | 235 | 76.8 |
| 6 | 1732 | 90.9 | 687 | 163 |
| 8 | 1893 | 111 | 1172 | 169 |
| 10 | — | — | 1568 | 144 |

EXAMPLE 8

To examine the skin permeativities of other medicines to an l-menthol-ethanol-water system, formulations using fentanyl citrate (FTC), eptazocine hydrobromide (ETH), cocaine hydrochloride (CCH), and morphine hydrochloride were prepared and examined for percutaneous absorbability.

TABLE 15 unit: w %

| Sample Component | This Invention | | | |
|---|---|---|---|---|
| | 1 | 14 | 15 | 16 |
| Morphine hydrochloride | 1 | — | — | — |
| FTC | — | 1 | — | — |
| ETH | — | — | 1 | — |
| CCH | — | — | — | 1 |
| l-Menthol | 5 | 5 | 5 | 5 |
| Ethanol | 40 | 40 | 40 | 40 |
| Water | 54 | 54 | 54 | 54 |

Figure 8A:
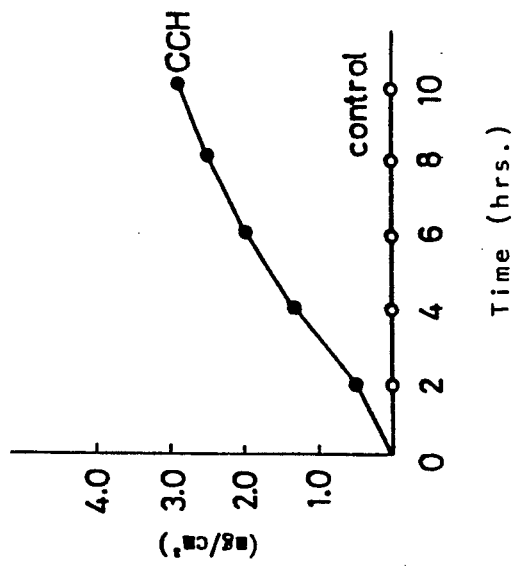
Figure 8B:
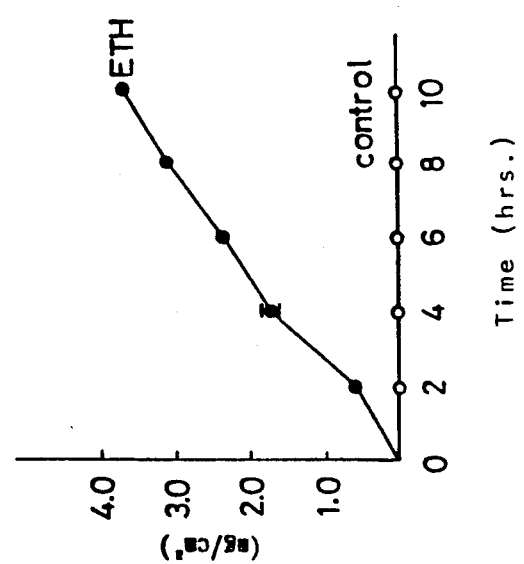
Figure 8C:
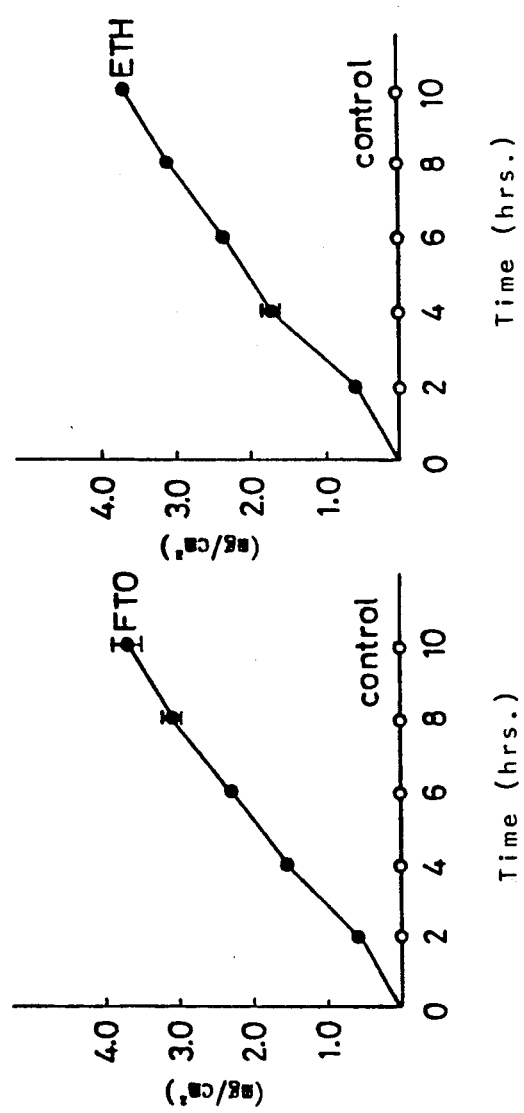

As shown in FIG. 8(a), FIG. 8(b) and FIG. 8(c) and Table 16, the results showed that every formulation is excellent in skin permeativity in the l-menthol-ethanol-water system, i.e., FTC, sample 14, FIG. 8(a);
ETH, sample 15, FIG. 8(b), and
CCH, sample 16, FIG. 8(c).

TABLE 16 unit: μg/cm²

| Time elapsed | This Invention 1 | | This Invention 14 | | This Invention 15 | | This Invention 16 | |
|---|---|---|---|---|---|---|---|---|
| | Mean | Deviation | Mean | Deviation | Mean | Deviation | Mean | Deviation |
| 2 | 629 | 20.9 | 570 | 19.5 | 586 | 61.7 | 495 | 11.2 |
| 4 | 1436 | 87.3 | 1539 | 56.4 | 1729 | 87.8 | 1353 | 13.7 |
| 6 | 1732 | 90.9 | 2274 | 66.9 | 2349 | 57.9 | 2018 | 40.4 |
| 8 | 1893 | 111 | 3086 | 122 | 3095 | 52.0 | 2549 | 14.3 |
| 10 | — | — | 3692 | 187 | 3691 | 50.7 | 2694 | 38.1 |

EXAMPLE 9

To examine the effect of different concentration of l-menthol on skin permeativity of eptazocine hydrobromide from an l-menthol-ethanol-water system, formulations as shown in Table 17 were prepared and examined for percutaneous absorbability.

TABLE 17 unit: w %

| Sample Component | This Invention | | |
|---|---|---|---|
| | 17 | 18 | 15 |
| E.T.H. | 1 | 1 | 1 |
| l-Menthol | 1 | 2 | 5 |
| Ethanol | 40 | 40 | 40 |
| Water | 58 | 57 | 54 |

Figure 9:
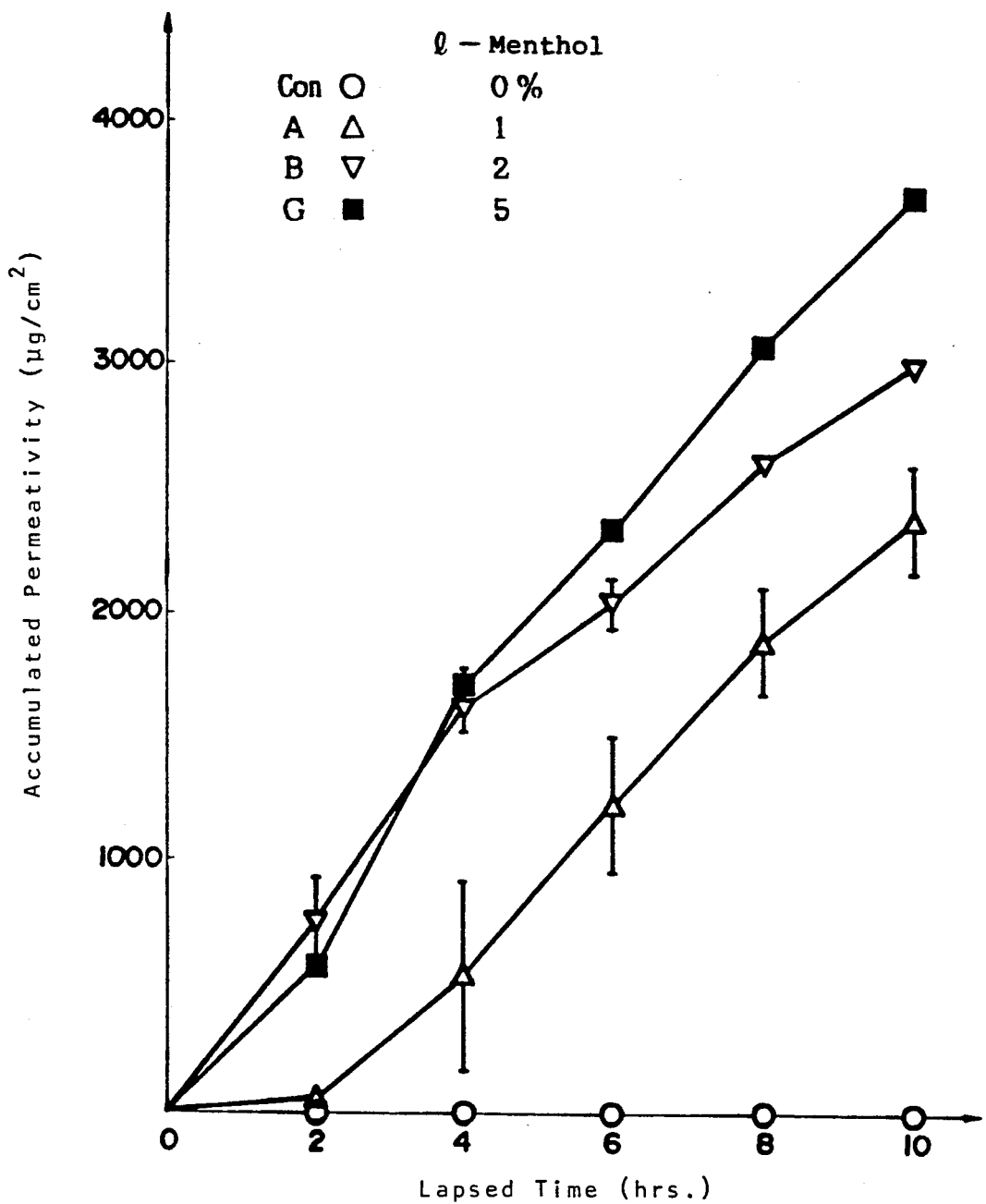

As shown in FIG. 9 and Table 18, the results showed that skin permeativity is excellent when the concentration of menthol is 1.0 wt. % or more.

TABLE 18

| | | | unit: μg/cm² | | | |
|---|---|---|---|---|---|---|
| Time | This Invention 17 | | This Invention 18 | | This Invention 15 | |
| elapsed | Mean | Deviation | Mean | Deviation | Mean | Deviation |
| 2 | 55.03 | 67.10 | 669.7 | 170.8 | 586.3 | 61.70 |
| 4 | 556.3 | 380.3 | 1638 | 117.0 | 1729 | 87.77 |
| 6 | 1264 | 275.4 | 2063 | 99.52 | 2349 | 57.93 |
| 8 | 1922 | 223.9 | 2623 | 36.51 | 3095 | 52.03 |
| 10 | 2407 | 170.8 | 3017 | 44.86 | 3691 | 50.61 |

EXAMPLE 10

To examine the effect of the concentration of ethanol on skin permeativity of eptazocine hydrobromide from an l-menthol-ethanol-water system, formulations as shown in Table 19 were prepared and examined for percutaneous absorbability.

TABLE 19

| | unit: w % | | |
|---|---|---|---|
| Sample | This Invention | | |
| Component | 19 | 20 | 15 |
| E.T.H. | 1 | 1 | 1 |
| l-Menthol | 5 | 5 | 5 |
| Ethanol | 10 | 20 | 40 |
| Water | 84 | 73 | 54 |

As shown in FIG. 10 and Table 19, the results showed that skin permeativity is excellent when the concentration of ethanol is 10 wt. % or more.

TABLE 20

| | | | unit: μg/cm² | | | |
|---|---|---|---|---|---|---|
| Time | This Invention 19 | | This Invention 20 | | This Invention 15 | |
| elapsed | Mean | Deviation | Mean | Deviation | Mean | Deviation |
| 2 | 9.121 | 9.592 | 97.25 | 14.79 | 586.3 | 61.70 |
| 4 | 127.3 | 78.04 | 324.6 | 187.0 | 1729 | 87.77 |
| 6 | 393.5 | 207.5 | 1138 | 195.9 | 2349 | 57.93 |
| 8 | 755.6 | 303.4 | 1599 | 243.3 | 3095 | 52.03 |
| 10 | 1170 | 276.0 | 2152 | 422.4 | 3691 | 50.61 |

EXAMPLE 11

To examine the effect of concentration of eptazocine hydrobromide on skin permeativity of eptazocine hydrobromide from an l-menthol-ethanol-water system, formulations as shown in Table 21 were prepared and examined for percutaneous absorbability.

TABLE 21

| | unit: w % | | |
|---|---|---|---|
| Sample | This Invention | | |
| Component | 21 | 22 | 15 |
| E.T.H. | 0.1 | 5 | 1 |
| l-Menthol | 5 | 5 | 5 |
| Ethanol | 40 | 40 | 40 |
| Water | 54.9 | 50 | 54 |

Figure 11:
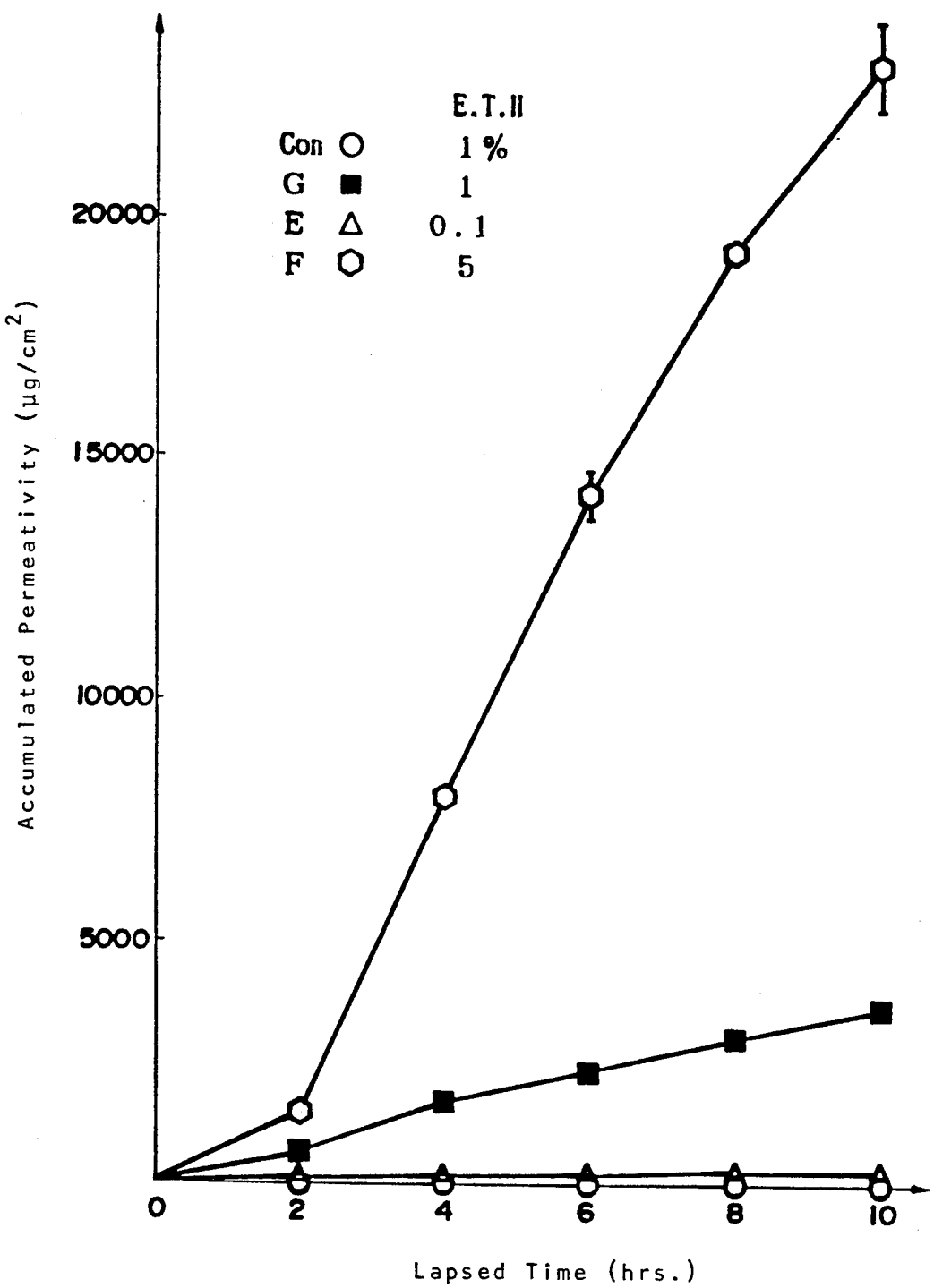

As shown in FIG. 11 and Table 22, the results showed that skin permeativity is excellent when the concentration of eptazocine bromohydride is 1.0 wt. % or more.

TABLE 22

| | | | unit: μg/cm² | | | |
|---|---|---|---|---|---|---|
| Time | This Invention 19 | | This Invention 20 | | This Invention 15 | |
| elapsed | Mean | Deviation | Mean | Deviation | Mean | Deviation |
| 2 | 53.82 | 2.934 | 1418 | 586.3 | 586.3 | 61.70 |
| 4 | 132.2 | 13.47 | 8013 | 328.3 | 1729 | 87.77 |
| 6 | 206.1 | 26.52 | 14273 | 549.4 | 2349 | 57.93 |
| 8 | 268.2 | 23.03 | 19415 | 103.5 | 3095 | 52.03 |
| 10 | 311.0 | 27.65 | 23300 | 913.5 | 3691 | 50.61 |

INDUSTRIAL APPLICABILITY

The percutaneous absorption accelerating formations according to the present invention allow the administration from the skin for medicines which could not be administered from the skin in the past by adapting monoterpenes which were only used as perfumes as percutaneous absorption accelerators and lower alcohols having 1-5 carbon atoms as skin absorption accelerating assistants, and combining them.

As the prevent invention is constituted for percutaneous absorption, formulations having long analgesic effects can be provided.

The formulations according to the present invention are suitable for at-home treatment because of their easy recipe, compared with injecting agents and oral agents, and excellent in persistency.

What is claimed is:

1. A composition which is percutaneously absorbable, comprising:
    a narcotic analgesic selected from the group consisting of morphine and analogous analgesics thereof;

from 1 to 20 weight percent of a percutaneous absorption accelerator comprised of one of (a) a terpene and (b) an essential oil;

from 10 to 60 weight percent of a percutaneous absorption accelerating assistant comprised of one of (a) a lower alcohol having 1-5 carbon atoms, (b) water and (c) a lower glycol having 2-5 carbon atoms.

2. The composition according to claim 1, wherein the percutaneous absorption accelerator is one of (a) a monoterpene and (b) an essential oil containing a monoterpene.

3. The composition according to claim 2, wherein the percutaneous absorption accelerator is a monoterpene and is one of (a) l-menthol and (b) terpineol.

4. The composition according to claim 3, wherein the percutaneous absorption accelerating assistant is at least one lower alcohol having 1-5 carbon atoms selected from the group consisting essentially of methyl alcohol, ethyl alcohol, propyl alcohol, isopropyl alcohol, butyl alcohol, or amyl alcohol.

5. The composition according to claim 2, wherein the percutaneous absorption accelerator is an essential oil containing a monoterpene and is one of (a) mentha oil and (b) peppermint oil.

6. The composition according to claim 5, wherein the percutaneous absorption accelerating assistant is at least one lower alcohol having 1-5 carbon atoms selected from the group consisting essentially of methyl alcohol, ethyl alcohol, propyl alcohol, isopropyl alcohol, butyl alcohol, and amyl alcohol.

7. The composition according to claim 2, wherein the percutaneous absorption accelerating assistant is at least one lower alcohol having 1-5 carbon atoms selected from the group consisting essentially of methyl alcohol, ethyl alcohol, propyl alcohol, isopropyl alcohol, butyl alcohol, and amyl alcohol.

8. The composition according to claim 1, wherein the percutaneous absorption accelerating assistant is at least one lower alcohol having 1-5 carbon atoms selected from the group consisting essentially of methyl alcohol, ethyl alcohol, propyl alcohol, isopropyl alcohol, butyl alcohol, or amyl alcohol.

9. The composition according to claim 1, wherein the analogous analgesics of morphine include salts of morphine and bases of morphine.

10. The composition according to claim 9, wherein the analogous analgesics of morphine are selected from the group consisting essentially or morphine hydrochloride, ethyl morphine hydrochloride, and morphine sulfate.

* * * * *